(12) United States Patent
Li et al.

(10) Patent No.: US 10,302,578 B2
(45) Date of Patent: May 28, 2019

(54) METHOD FOR PERFORMING MATERIAL DECOMPOSITION USING A DUAL-ENERGY X-RAY CT AND CORRESPONDING DUAL-ENERGY X-RAY CT APPARATUS

(71) Applicants: Tsinghua University, Beijing (CN); Nuctech Company Limited, Beijing (CN)

(72) Inventors: Liang Li, Beijing (CN); Zhiqiang Chen, Beijing (CN); Kejun Kang, Beijing (CN); Li Zhang, Beijing (CN); Ziran Zhao, Beijing (CN); Yuxiang Xing, Beijing (CN); Jianmin Li, Beijing (CN); Yulan Li, Beijing (CN); Tiao Zhao, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 256 days.

(21) Appl. No.: 15/494,884

(22) Filed: Apr. 24, 2017

(65) Prior Publication Data
US 2017/0328844 A1    Nov. 16, 2017

(30) Foreign Application Priority Data
May 10, 2016    (CN) .......................... 2016 1 0304724

(51) Int. Cl.
*G01N 23/046* (2018.01)
*G01N 23/087* (2018.01)

(52) U.S. Cl.
CPC ......... *G01N 23/087* (2013.01); *G01N 23/046* (2013.01); *G01N 2223/206* (2013.01); *G01N 2223/419* (2013.01); *G01N 2223/423* (2013.01)

(58) Field of Classification Search
CPC ............... G01N 23/087; G01N 23/046; G01N 2223/206; G01N 2223/419; G01N 2223/423
(Continued)

(56) References Cited

U.S. PATENT DOCUMENTS

2009/0052621 A1    2/2009    Walter et al.
2009/0262997 A1    10/2009    Zou et al.
(Continued)

FOREIGN PATENT DOCUMENTS

EP        2437050 A1    4/2012

OTHER PUBLICATIONS

"Search and Exam Report dated Sep. 29, 2017", (Sep. 29, 2017), 5 pgs.

*Primary Examiner* — Courtney D Thomas
(74) *Attorney, Agent, or Firm* — Schwegman Lundberg & Woessner, P.A.

(57) ABSTRACT

Methods and system for decomposing a high-energy dual-energy X-ray CT material are disclosed. In the method, two types of effect such as Compton effect and electron pairing effect which dominates are reserved and the influence of the other effect such a photoelectric effect is removed so as to improve the accuracy of the material decomposition. The unique advantage of the present disclosure is to effectively remove the error of the calculated atomic number Z due to directly selecting two effects during processes of material decomposition in the conventional dual-energy CT method. This may greatly improve the accuracy of dual-energy CT identification of the material, and it is important to improve the conventional dual-use CT imaging system applications, such as clinical therapy, security inspection, industrial non-destructive testing, customs anti-smuggling and other fields.

20 Claims, 5 Drawing Sheets

(58) Field of Classification Search
USPC .......................................... 378/4–20, 57, 62
See application file for complete search history.

(56) References Cited

U.S. PATENT DOCUMENTS

2012/0069952 A1* 3/2012 Wu ..................... A61B 6/032
378/5
2016/0287205 A1* 10/2016 Zou ..................... A61B 6/585

\* cited by examiner

METHOD FOR PERFORMING MATERIAL DECOMPOSITION USING A DUAL-ENERGY X-RAY CT AND CORRESPONDING DUAL-ENERGY X-RAY CT APPARATUS

CROSS-REFERENCE TO RELATED APPLICATION(S)

The present disclosure claims priority to a Chinese Application No. 201610304724.4 filed on May 10, 2016, which is incorporated herein by reference in its entirety.

TECHNICAL FIELD

The present disclosure relates to radiation imaging and in particular to methods for performing material decomposition using a dual-energy X-ray CT (Computerized Tomography) and corresponding dual-energy X-ray CT apparatuses.

BACKGROUND

X-ray CT imaging technology has been widely used in clinical therapy, security inspection and industrial nondestructive testing and other fields. Currently, mainstream CT technology uses a single X-ray energy spectrum, and an energy integral detector is utilized to obtain a distribution image of linear attenuation coefficient inside the scanning object by using CT reconstruction method. The distribution image of linear attenuation coefficient is a grayscale image reflecting X-ray absorption intensity of the material and cannot meet a requirement of accurate identification of the material for the clinical therapy and security inspection. The emergence of dual-energy X-ray CT technology provides a more powerful way to achieve accurate material identification. The dual-energy CT may reconstruct to get distribution images of an atomic number Z and electron density $\rho_e$ the object being scanned by collecting projection data under two different X-ray spectra which is usually recorded as low-energy data and high-energy data and calculating through a special dual-energy CT material decomposition algorithm.

As an attenuation coefficient of the material varies with change of the photon energy, the most common X-ray source in X-ray CT is X-ray machine or accelerator, the X-ray emitted from which has a wide spectrum and is not monochrome. Therefore, a projection model of a traditional CT should be nonlinear. The equivalent attenuation coefficient is obtained by directly reconstructing the projection data, which is an average value of the linear attenuation coefficient function commonly affected by the radiation source spectrum and the radiated object, and does not have a clear physical meaning and may only provide structure information of the radiated object. In contrast, the dual-energy CT obtains two sets of projection data by utilizing two different X-ray spectrums and implements material identification through a special dual-energy CT material decomposition method.

The dual-energy CT decomposition algorithm may be divided into three categories: a projection domain pre-processing method, an image domain post-processing method and an iterative method. The projection domain pre-processing method considers that the linear attenuation coefficient function may be decomposed into a linear combination of two known basic functions which only take energy as variables. For each of ray paths, an integral value of the linear combination on the ray path is calculated by using the dual-energy projection value on the pat, and then the combined coefficients of each point are obtained according to the traditional CT image reconstruction algorithm, which corresponds to feature quantity of the linear attenuation coefficient function at each point. The linear attenuation coefficient function or substance information (atomic number and electron density) of such a point may be determined according to the feature quantity. The projection domain pre-processing method may effectively remove hardened artifacts, but requires dual-projection path matching. The image domain post-processing method firstly reconstructs the projection data of the dual-energy CT respectively to obtain reconstructed CT images at two different energy spectrums and then compares the reconstruction value of each pixel and the basis material image to complete the material decomposition. The image domain post-processing method is simple to implement, but cannot remove hardened artifacts. The iterative method is to integrate CT image reconstruction and material decomposition into one mathematical model. The iterative method may be used to complete the final material decomposition, and the iterative method may also add other priori constraints, such as statistical noise model, and may optimize the iterative solution with maximum likelihood (ML), Maximum expectation (EM) or maximum a posteriori (MAP). The advantage of the iterative method is that it may better suppress noise, but its computational process is more complex and time consuming.

In the dual-energy X-ray CT imaging, the theoretical basis for the three kinds of material decomposition methods as mentioned above is interaction of X-ray and the substance. Considering that the X-ray energy applied in fields such as clinical therapy, security inspection, industrial non-destructive testing and custom smuggling detection ranges between 10 keV~10 MeV, there are four possible interactions: Rayleigh scattering, photoelectric effect, Compton scattering and electron pairing effect, which may completely describe the attenuation coefficient function of many substances. In practice, since the dual-energy CT only collects projection data of the high and low energy, the dual-energy CT may only use the mathematical model of two interactions to decompose the material, and ignore the effects of other interactions. For example, in the low-energy imaging, only the photoelectric effect and Compton scattering are considered, while in the high-energy imaging only the Compton scattering and electron pairing effects are considered. Although these approximations enable the dual-energy CT imaging to decompose the material, it will inevitably bring some error, and in some cases these error becomes nonignorable. Especially in the high-energy dual-energy CT imaging, such as the detection of radioactive nuclear materials, large van container inspection system, air box inspection system, and large metal work piece nondestructive testing and so on, the cross-section of the electron pairing effect is not much larger than that of the photoelectric effect. If only one method is taken into consideration, it will have to bring obvious errors and different effects on the decomposition of materials have to be considered to effectively improve the effect of high-energy dual-energy CT imaging.

SUMMARY

In view of one or more disadvantages in conventional approaches, methods for performing material decomposition using a dual-energy X-ray CT and corresponding X-ray apparatuses have been proposed.

In one aspect of the present disclosure, there is provided a method for performing material decomposition using a dual-energy X-ray CT, the dual-energy X-ray CT performing a dual-energy X-ray scanning on an object to be inspected to obtain a high energy projection data and a low energy projection data, the method comprising steps of: performing a dual-energy base material decomposition with respect to the high-energy projection data and the low-energy projection data, so as to obtain base material decomposition coefficients; calculating atomic number distribution and electron density distribution for the object to be inspected, with the base material decomposition coefficients as initial values; calculating a mass attenuation coefficient corresponding to the photoelectric effect according to the atomic number distribution and electron density distribution; correcting the high energy projection data and the low energy projection data utilizing the mass attenuation coefficient corresponding to the photoelectric effect to remove a portion of the high energy projection data and the low energy projection data corresponding to the photoelectric effect; obtaining corrected base material decomposition coefficients using corrected high energy projection data and low energy projection data; and obtaining final atomic number distribution and electron density distribution for the object to be inspected utilizing the corrected base material decomposition coefficients.

In one embodiment, the step of obtaining final atomic number distribution and electron density distribution for the object to be inspected utilizing the corrected base material decomposition coefficients further comprises: determining whether the corrected base material decomposition coefficients satisfy an iteration convergence criterion; on the condition that the corrected base material decomposition coefficients satisfy the iteration convergence criterion, calculating corrected atomic number distribution and electron density distribution for the object to be inspected as the final atomic number distribution and electron density distribution by utilizing the corrected base material decomposition coefficients.

In one embodiment, the method further comprises: on the condition that the corrected base material decomposition coefficients do not satisfy the iteration convergence criterion, iterating with the corrected base material decomposition coefficients as the initial values until the iteration convergence criterion is satisfied by further corrected base material decomposition coefficients; calculating corrected atomic number distribution and electron density distribution for the object to be inspected as the final atomic number distribution and electron density distribution by utilizing the further corrected base material decomposition coefficients that satisfy the iteration convergence criterion.

In one embodiment, the final atomic number distribution and electron density distribution include equivalent atomic number and electron density for each pixel.

In one embodiment, the base material decomposition coefficients are reconstructed using filtering back projection or algebra reconstruction technique iterative algorithms.

In another aspect of the present disclosure, there is provided a method for performing material decomposition using a dual-energy X-ray CT, the dual-energy X-ray CT performing a dual-energy X-ray scanning on an object to be inspected to obtain a high energy projection data and a low energy projection data, the method comprising steps of: performing a dual-energy base material decomposition with respect to the high-energy projection data and the low-energy projection data, so as to obtain base material decomposition coefficients; calculating atomic number distribution and electron density distribution for the object to be inspected, with the base material decomposition coefficients as initial values; calculating a mass attenuation coefficient corresponding to the Rayleigh scattering effect according to the atomic number distribution and electron density distribution; correcting the high energy projection data and the low energy projection data utilizing the mass attenuation coefficient corresponding to the Rayleigh scattering effect to remove a portion of the high energy projection data and the low energy projection data corresponding to the Rayleigh scattering effect; obtaining corrected base material decomposition coefficients using corrected high energy projection data and low energy projection data: and obtaining final atomic number distribution and electron density distribution for the object to be inspected utilizing the corrected base material decomposition coefficients.

In a further aspect of the present disclosure, there is provided a dual-energy X-ray CT apparatus comprising: an X-ray source configured to perform a dual-energy X-ray scanning on an object to be inspected; a detecting and collecting device configured to receive dual-energy X-rays passing through the object to be inspected so as to generate a high energy projection data and a low energy projection data; a calculation unit configured to perform the following operations: performing a dual-energy base material decomposition with respect to the high-energy projection data and the low-energy projection data, so as to obtain base material decomposition coefficients; calculating atomic number distribution and electron density distribution for the object to be inspected, with the base material decomposition coefficients as initial values; calculating a mass attenuation coefficient corresponding to the photoelectric effect according to the atomic number distribution and electron density distribution; correcting the high energy projection data and the low energy projection data utilizing the mass attenuation coefficient corresponding to the photoelectric effect to remove a portion of the high energy projection data and the low energy projection data corresponding to the photoelectric effect; obtaining corrected base material decomposition coefficients using corrected high energy projection data and low energy projection data; and obtaining final atomic number distribution and electron density distribution for the object to be inspected utilizing the corrected base material decomposition coefficients.

In another aspect of the present disclosure, there is provided a dual-energy X-ray CT apparatus comprising: an X-ray source configured to perform a dual-energy X-ray scanning on an object to be inspected; a detecting and collecting device configured to receive dual-energy X-rays passing through the object to be inspected so as to generate a high energy projection data and a low energy projection data; a calculation unit configured to perform the following operations; performing a dual-energy base material decomposition with respect to the high-energy projection data and the low-energy projection data, so as to obtain base material decomposition coefficients; calculating atomic number distribution and electron density distribution for the object to be inspected, with the base material decomposition coefficients as initial values; calculating a mass attenuation coefficient corresponding to the Rayleigh scattering effect according to the atomic number distribution and electron density distribution; correcting the high energy projection data and the low energy projection data utilizing the mass attenuation coefficient corresponding to the Rayleigh scattering effect to remove a portion of the high energy projection data and the low energy projection data corresponding to the Rayleigh scattering effect; obtaining corrected base material decomposition coefficients using corrected high energy projection data and low energy projection data and obtaining final atomic number distribution and electron density distribution for the object to be inspected utilizing the corrected base material decomposition coefficients.

The embodiments of the above embodiments may be utilized to effectively remove the error of the calculated atomic number Z due to directly neglecting some effect during processes of material decomposition and substance identification in the conventional dual-energy CT method. This may greatly improve the accuracy of dual-energy CT identification of the material, and it is important to improve the conventional dual-use CT imaging system applications, such as clinical therapy, security inspection, industrial non-destructive testing, customs anti-smuggling and other fields.

BRIEF DESCRIPTION OF THE DRAWINGS

In order to better understand the present disclosure, an embodiment of the present disclosure will be illustrated with reference to the following drawings, in which.

The drawings do not show all of the circuit or structure. Throughout the drawings, like reference numerals refer to like or similar parts or features.

DETAILED DESCRIPTION

Specific embodiments of the present disclosure will be described in detail below and please note that the embodiments described herein are used for the purpose of exemplification rather than limitation of the present disclosure. Hereinafter, to provide a thorough understanding of the present disclosure, numerous specific details are set forth. However, it would be obvious for one ordinarily skilled in the art that the present disclosure may be practiced without these specific details. In other examples, known structures, materials, or methods are not described in detail to avoid any possible obfuscation of the present disclosure.

Throughout the specification, the reference to "an embodiment", "the embodiment", "an example", or "the example" is meant that a specific feature, structure, or feature described with reference to this embodiment or example is contained by at least one embodiment of the present disclosure. Therefore, the phrases "in an embodiment", "in the embodiment", "an example", or "the example" throughout the specification is not necessarily intended to refer to a same embodiment or example. Further, specific features, structures, or characteristics may be combined into one or more embodiments or examples in any suitable combination and/or sub-combination. Further, it is appreciated by one ordinarily skilled in the art that the term "and/or" used herein comprises any and all combinations of one or more related items that are listed.

Figure 1:
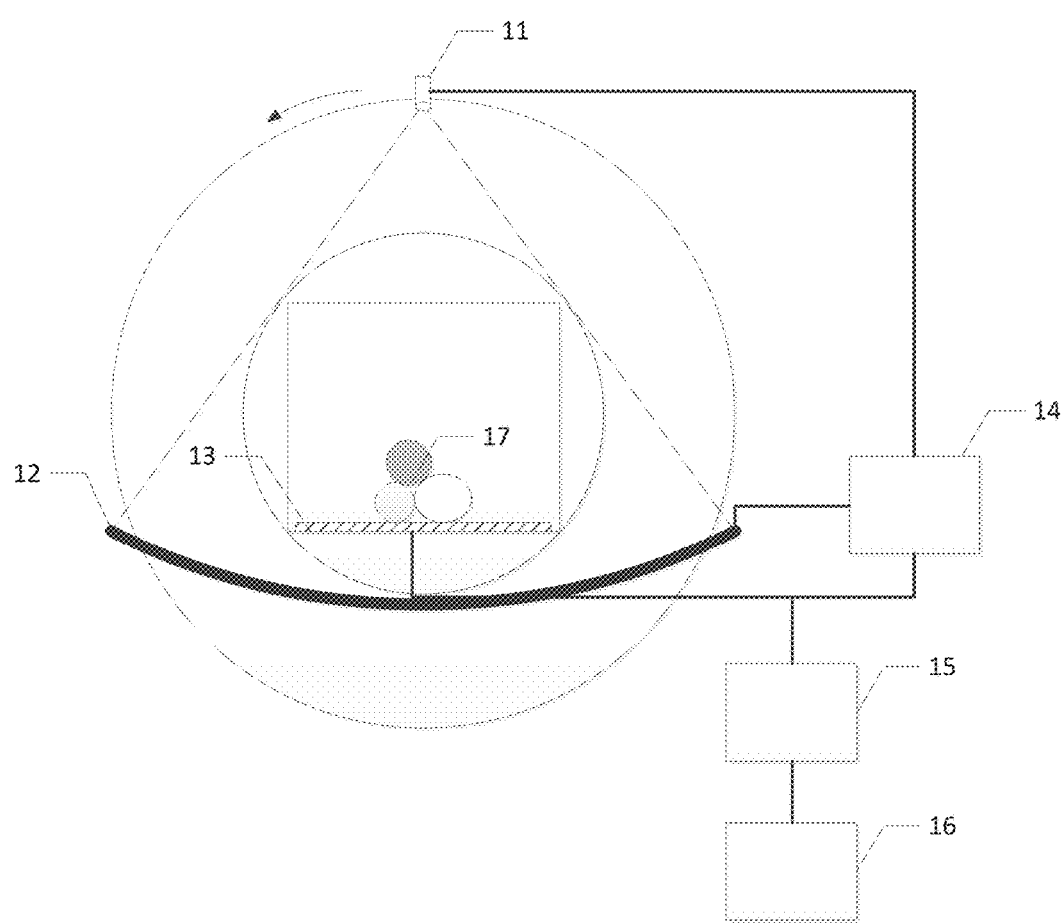
FIG. 1 shows a schematic block diagram of a dual-energy X-ray CT system according to an embodiment of the present disclosure.

FIG. 1 shows a schematic structural view of a CT system according to an embodiment of the present disclosure. As shown in FIG. 1, the CT system according to the present embodiment includes an X-ray source 11, a detecting and collecting device 12, a transferring device 13, a controller 14, a calculation unit 15 (such as a CPU or a GPU), and a display unit 16. The X-ray source 11 and the detecting and collecting device 12 are mounted on a rotating device (such as a frame) and can rotate at a high speed under control of the controller 14. The controller 14 controls the transferring device 13 (such as a belt) to transfer the inspected object 17 from one side of the rotating device to another side at a constant rate. The X-ray source 11 emits high-energy/low-energy rays through the object 17. The ray is then received by the detector and is converted by the analog-to-digital conversion circuit to a digital signal as the projection data. The calculation unit 15 (such as an image processing unit) reconstructs the digital signal into a three-dimensional image reflecting the internal structure and/or material characteristics of the object 17.

According to an embodiment of the present disclosure, the X-ray source 11 may be a dual-energy X-ray source, and the detecting and collecting device 12 may receive X-rays with various energies to perform dual-energy X-ray inspection of the object 17 to be inspected. The performed scanning may be a spiral scanning or other scanning. The dual-energy X-ray CT imaging methods comprises the following categories: 1) two or more different energy spectrum X-ray source are used, and the typical technology includes a dual-source CT technology, an X-ray machine high pressure and fast switching technology and a K edge filter method 2) a detector with X-ray energy resolution is utilized, such as a double-layer detector or photon counting detector. The above two kinds of technology may be applied in clinical therapy, security inspection, customs anti-smuggling, industrial non-destructive testing and other fields. The technique of the present disclosure may be applied to any of the above mentioned dual-energy X-ray CT imaging system, whether it is low energy (keV level) or high energy (MeV level).

The detecting and collecting device 12 is, for example, a detector and a data collector with an integrated module structure, such as a flat panel detector. The detecting and collecting device 12 is utilized for detecting the rays transmitted through the object to obtain an analog signal, and for converting the analog signal into a digital signal to output projection data of the object for the X-ray.

The controller 14 is connected to the X-ray source 11, the detecting and collecting device 12 and the transferring device 13 to control the respective parts of the system to be synchronously operated. The calculation unit 15 is used to process the data collected by the data collector, to process and reconstruct the data and to output results. For example, after the object 17 is scanned by the dual-energy CT device, the obtained dual-energy three-dimensional image data is input to the calculation unit 15. The mounted substance identification system is used to identify the object based on the image data to get the equivalent atomic number and density for different substances, and to color the three-dimensional image to be displayed on the screen of the display unit 16 for being inspected by an image judger.

As shown in FIG. 1, the X-ray source 11 is placed on one side of the object 17 to be inspected, and the detecting and collecting device 12 is placed on the other side of the object 17 and includes a detector and a data collector for acquiring a multi-angle projection data of the object 17. The data collector includes a data amplifying and shaping circuit which may operate in a (current) integral mode or a pulse (counting) mode. A data output cable of the detecting and collecting device 12 is connected to the controller 14 and the calculation unit 15, and the acquired data is stored in a memory according to a trigger command. It will be appreciated by those skilled in the art that in other embodiments the ray source and the detector may employ non-frame mode, i.e. static distributed multi-light sources.

According to the Beer-Lambert theorem, after a beam of X-ray with a certain spectral distribution is attenuated by an object, the intensity of the signal collected on the energy-integral detector may be described by the following formula:

$$I = \int I_0(E) e^{-\int_{l(\vec{x})} \mu(\vec{x},E) d\vec{x}} dE, \quad (1)$$

where $\mu(\vec{x},E)$ represents a linear attenuation function of the object at a point $\vec{x}$ for the X-ray with an energy of E; $I_0(E)$ represents an intensity of the signal of the photons with an energy of E in the beam of X-rays which is directly incidence onto the detector without passing any objects and is collected; and $l(\vec{x})$ represents a path of the X-ray.

During a process of the dual-energy X-ray CT imaging, the base material decomposition model is often used to decompose the material, and a basic principle of the base material decomposition model is that the linear attenuation coefficient of all the substances may be determined uniquely by two variables of the atomic number and the electron density. Therefore, two kinds of base materials, such as carbon and iron, may be selected and a linear combination of the line attenuation coefficients of the base material may be utilized to represent the line attenuation coefficient for all of other materials, i.e.:

$$\mu(E) = b_1 \mu_1(E) + b_1 \mu_2(E) \quad (2),$$

where $\mu(E)$ is the linear attenuation coefficient of the scanned object at any point of, $\mu_1(E)$ and $\mu_2(E)$ are the linear attenuation coefficient functions of the two known base materials, and $b_1$ and $b_2$ are the decomposition coefficients of the base materials at that point.

The following equation may be derived by substituting the equation (2) into the equation (1):

$$I = \int I_0(E) e^{-\int_{l(\vec{x})} b_1 \mu_1(E) + b_2 \mu_2(E) d\vec{x}} dE. \quad (3)$$

Considering that $\mu_1(E)$ and $\mu_2(E)$ are known quantities which are independent of position, the above equation may be further simplified as:

$$I = \int I_{L0}(E) e^{-\mu_1(E) B_1 - \mu_2(E) B_2} dE \quad (4)$$

$$B_1 = \int_{l(\vec{x})} b_1 d\vec{x}, \; B_2 = \int_{l(\vec{x})} b_2 d\vec{x}. \quad (5)$$

During a process of the dual-energy X-ray CT imaging, the projection data at two different energy spectrums are generally collected and are recorded as a high-energy projection data and a low-energy projection data as follows:

$$\begin{cases} I_L = \int_0^{E_L} I_{L0}(E) e^{-\mu_1(E) B_1 - \mu_2(E) B_2} dE \\ I_H = \int_0^{E_H} I_{H0}(E) e^{-\mu_1(E) B_1 - \mu_2(E) B_2} dE \end{cases} \quad (6)$$

The terms of $B_1$ and $B_2$ are similarly defined as those of the equation (5).

In the field of clinical imaging, photon energy of the used X-ray is generally no more than 160 keV. In this energy range, there are three main interaction modes of the photon and the substance: Rayleigh scattering, photoelectric effect and Compton scattering. The base material decomposition methods currently widely used in the clinical dual-energy CT (often called as energy spectrum CT) are all based on the photoelectric effect and the Compton scattering, with the Rayleigh scattering being neglected. This approximation will introduce error.

In the field of custom inspection and industrial imaging, such as airframe CT imaging, the thickness of the illuminated object tends to be thicker and the atomic number varies widely, which requires strong rays to image. Usually an accelerator is utilized as a ray source and the photon energy ranges from 100 keV to several MeV even more than a dozen MeV. In such an energy range, there are three interaction modes of the photon and the substance: photoelectric effect, Compton scattering effect and electron pairing effect, and each of them cannot be completely ignored. Therefore, in the base material method, the mass attenuation coefficient functions of the three kinds of base materials are required to describe the mass attenuation coefficient function of any substances. However, the dual-energy CT can only provide two equations and the number of variables is more than the number of equations, so the decomposition problem is indefinite and unable to be solved. Therefore, the conventional X-ray high-energy dual-energy CT will ignore one of the interaction modes and apply the dual-energy base materials decomposition method to the remaining ones. This does not match with the physical model and results in significant errors in the decomposition results.

Hereinafter, the material decomposition method of the present disclosure will be illustrated in detail with reference to a high-energy dual-energy CT having an X-ray energy range of dozens of keV to a dozen of MeV.

According to an iterative base material decomposition method provided by the present disclosure, for example in the case of high-energy dual-energy CT, during the current iteration, the photoelectric contribution in the projection is estimated by the base material decomposition result obtained from the previous iteration, and then the photoelectric contribution is removed from the original projection to implement the base material decomposition to get the new base material decomposition results and enter the next iteration. In this iterative way, the photoelectric effect is separated from the three effects so that when the base material is decomposed, the mass attenuation coefficient function of the two kinds of base materials which removes the photoelectric effect is used as the basis function for the decomposition of the base material, and the contribution of the photoelectric effect is removed from the projection data corresponding. Thus, the decomposition of the base material matches the physical model of the two effects (Compton scattering and the electron pairing effect), which effectively improves the accuracy of the decomposition.

Figure 2:
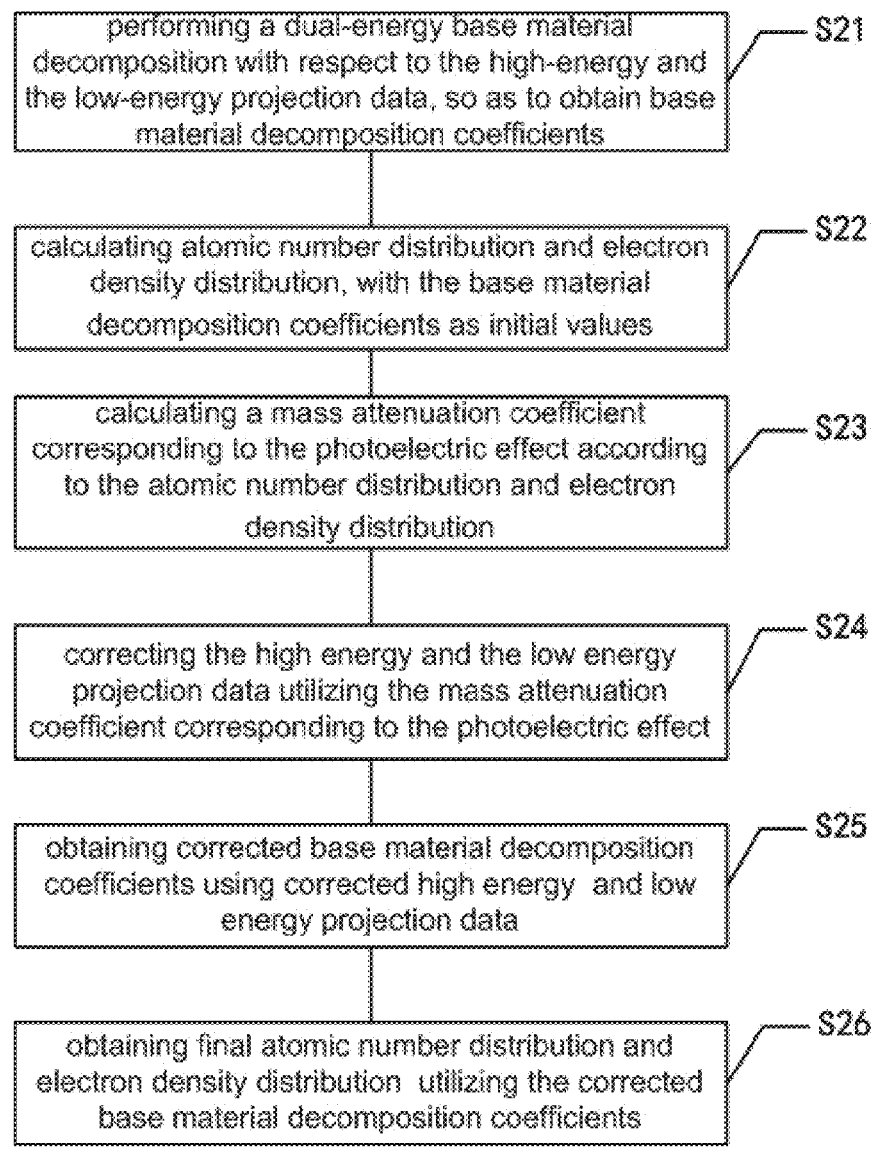
FIG. 2 is a flow diagram of a method for decomposing a material for dual-energy X-ray CT according to one embodiment of the present disclosure.

FIG. 2 is a flow diagram of a method for decomposing a material for dual-energy X-ray CT according to one embodiment of the present disclosure, where the dual-energy X-ray CT performs a dual-energy X-ray scanning on an object to be inspected to obtain a high energy projection data and a low energy projection data. As shown in FIG. 2, at a step of S21, a dual-energy X-ray scanning is performed on the object to be inspected to obtain a high-energy projection data and a low-energy projection data. At a step of S22, the dual-energy base material is decomposed for the high energy projection data and the low energy projection data to obtain a base material decomposition coefficient. For example, the high and low energy projection data collected by the dual-energy X-ray CT are pre-processed to get the following equation:

$$\begin{cases} p_L = -\log\frac{I_L}{I_{L0}} = -\log\left(\int_0^{E_L} D_{L0}(E)e^{-\mu_1(E)B_1-\mu_2(E)B_2}dE\right) \\ p_H = -\log\frac{I_H}{I_{H0}} = -\log\left(\int_0^{E_H} D_{H0}(E)e^{-\mu_1(E)B_1-\mu_2(E)B_2}dE\right) \end{cases} \quad (7)$$

In which $I_{L0}$ and $I_{H0}$ represent projection data of the low-energy X-rays and high-energy X-rays of the dual-energy CT directly incidence on a detector without passing through any objects, and $D_{L0}(E)$ and $D_{H0}(E)$ are normalized effective energy spectrum of the low energy and high energy X-ray source which is previously measured.

The formula (7) is converted into the nonlinear equation set as below:

$$f(B_1, B_2) = \begin{bmatrix} p_L + \log\left(\int_0^{E_L} D_{L0}(E)e^{-\mu_1(E)B_1-\mu_2(E)B_2}dE\right) \\ p_H + \log\left(\int_0^{E_H} D_{H0}(E)e^{-\mu_1(E)B_1-\mu_2(E)B_2}dE\right) \end{bmatrix}. \quad (8)$$

A nonlinear least square method, such as the Levenberg-Marquardt method is utilized to solve the following equation to obtain $B_1$ and $B_2$:

$$\min\frac{1}{2}f^T f \quad (9)$$

From $B_1$ and $B_2$, a CT image reconstruction algorithm such as a filtered back projection or ART (Algebra Reconstruction Technique) iterations or the like are utilized to reconstruct coefficients $b_1$ and $b_2$ for the base material decomposition. At this time, the calculated values of $b_1$ and $b_2$ are taken as initial values of the sequent iterative material decomposition.

At a step of S22, atomic number distribution and electron density distribution are calculated for the object to be inspected, with the base material decomposition coefficients as initial values. The final atomic number distribution and electron density distribution include equivalent atomic number and electron density for each pixel. For example, the equivalent atomic number and electron density of each pixels of the object to be scanned are calculated based on the initial value or the calculated $b_1$ and $b_2$ during the last iteration. The formula is as follows:

$$Z_{eff} = \frac{b_1 \cdot \rho_{e1} \cdot Z_1 + b_2 \cdot \rho_{e2} \cdot Z_2}{b_1 \cdot \rho_{e1} + b_2 \cdot \rho_{e2}}, \quad (10)$$

$$\rho_e = b_1 \cdot \rho_{e1} + b_2 \cdot \rho_{e2}. \quad (11)$$

Among them, $Z_1$ and $Z_2$ are the atomic number of the two kinds of materials, respectively, and $\rho_{e1}$ and $\rho_{e2}$ are the electron density of the two kinds of materials, which both are known quantities.

At a step of S23, a mass attenuation coefficient corresponding to the photoelectric effect are calculated according to the atomic number distribution and electron density distribution. For example, according to the equivalent atomic number and electron density of each pixel, a reaction cross-section and its corresponding mass attenuation coefficient for the photoelectric effect are calculated as follows:

$$\sigma_{pe}(Z_{eff}, E) = \frac{\sum_{i=1}^{4}\frac{a_i + b_i Z_{eff}}{c_i + d_i Z_{eff}}E^{-n_i}}{\sum_{i=1}^{4}\frac{a_i + b_i Z_{eff}}{c_i + d_i Z_{eff}}E_t^{-n_i}} \cdot \psi(Z_{eff}) \cdot 10^4 [\text{cm}^2], \quad (12)$$

$$\mu_{pe}(Z_{eff}, E) = \sigma_{pe}(Z_{eff}, E) \cdot \frac{\rho_e}{Z_{eff}} \cdot N_A, \quad (13)$$

where $N_A$ is the Avogadro constant, $E_t=0.1$ MeV, are known constants, $\psi(Z_{eff})$ is the photoelectric cross section of $Z_{eff}$ at the energy of $E_t$ and the unit is which is m$^2$, which is calculated by calculating a sum of the photoelectric cross sections of electrons at different shell layers (K layer, L layer, M layer, . . . ) by the following formula:

$$\psi(Z) = \frac{2^8 \pi e^2}{3 \text{ mc}} \frac{v_K^3}{v^4} \frac{\exp(-4\eta_K \tan^{-1}(1/\eta_K))}{1 - \exp(-2\pi\eta_K)} + \quad (14)$$

$$\frac{2^{11}\pi e^2}{2 \text{ mc}} \frac{v_L^3}{v^4}\left(1 + 3\frac{v_L}{v}\right)\frac{\exp(-8\eta_L \tan^{-1}(1/\eta_L))}{1 - \exp(-4\pi\eta_L)} +$$

$$\frac{2^{12}\pi e^2}{3 \text{ mc}} \frac{v_L^4}{v^5}\left(3 + 8\frac{v_L}{v}\right)\frac{\exp(-8\eta_L \tan^{-1}(1/\eta_L))}{1 - \exp(-4\pi\eta_L)} [\text{m}^2]$$

Among them, a number of parameters in the above equation (14) can be calculated as follows:

$$\begin{cases} \eta_K = \sqrt{\dfrac{v_K}{v - v_K}} \\ v_K = R_\infty c(Z - 0.3)^2 \\ \eta_L = \sqrt{\dfrac{v_L}{v - v_L}} \\ v_L = \dfrac{1}{4} R_\infty c(Z - 4.15)^2 \\ v = \dfrac{qE}{h} \\ R_\infty = \dfrac{2\pi^2 m e^4}{ch^3} \end{cases} \quad (15)$$

The constants in the above equation include: an elementary charge $e = 1.5189 \cdot 10^{-14}$ [$m^{3/2}$ $kg^{1/2} s^{-1}$], a charge quantity $q = 1.6021892 \cdot 10^{-19}$ [C], a stationary mass of electron $m = m_e = 9.1095 \cdot 10^{-31}$ [kg], a Planck constant $h = 6.6261 \cdot 10^{-34}$ [J·s], and a light speed $c = 2.99792458 \cdot 10^8$ [m/s].

At a step of S24, the mass attenuation coefficient corresponding to the photoelectric effect is utilized to correct the high-energy projection data and the low-energy projection data to remove the portions of the high-energy projection data and the low-energy projection data corresponding to the photoelectric effect. For example, the high and low energy projection data is corrected according to the mass attenuation coefficient corresponding to the photoelectric effect which is calculated based on the equation (13), the modification equation is shown as follows:

$$\begin{cases} p'_L = -\log\left(\int_0^{E_L} D'_{L0}(E) e^{-\mu_1(E)B_1 - \mu_2(E)B_2} dE\right) \\ p'_H = -\log\left(\int_0^{E_H} D'_{H0}(E) e^{-\mu_1(E)B_1 - \mu_2(E)B_2} dE\right) \end{cases} \quad (16)$$

In which, $D'_{L0}(E)$ and $D'_{H0}(E)$ can be deemed as an equivalent energy spectrum which correcting the photoelectric effect:

$$\begin{cases} D'_{L0}(E) = D_{L0}(E) \cdot e^{-\int_{l(\vec{x})} \mu_{pe}(\vec{x},E) d\vec{x}} \\ D'_{H0}(E) = D_{H0}(E) \cdot e^{-\int_{l(\vec{x})} \mu_{pe}(\vec{x},E) d\vec{x}} \end{cases} \quad (17)$$

At a step of S25, corrected base material decomposition coefficients are obtained using corrected high energy projection data and low energy projection data For example, the corrected high and low projection data (16) are substituted into the formula (8), and the Levenberg-Marquardt method is used to solve the nonlinear least-squares solution of equation (9) to get updated $B_1$ and $B_2$.

At a step of S26, final atomic number distribution and electron density distribution for the object to be inspected are obtained utilizing the corrected base material decomposition coefficients. From the above updated $B_1$ and $B_2$, the CT image reconstruction algorithm such as a filtered back projection or ART (Algebra Reconstruction Technique) iterations or the like are utilized to reconstruct updated coefficients $b_1$ and $b_2$ for the base material decomposition.

In one embodiment, at the step of S26, it is first to determine whether the corrected base material decomposition coefficients satisfy an iteration convergence criterion. If true, then corrected atomic number distribution and electron density distribution for the object to be inspected are calculated as the final atomic number distribution and electron density distribution by utilizing the corrected base material decomposition coefficients, where $b_1$ and $b_2$ are substituted into the formula (10-11).

If not true, the process proceeds to iterate with the corrected base material decomposition coefficients as the initial values until the iteration convergence criterion is satisfied by further corrected base material decomposition coefficients.

It should be noted that although the above derivation is developed for the X-ray high-energy dual-energy CT, the low-energy dual-energy CT decomposition of the material can be implemented in accordance with the above ideas. As to low-energy dual-energy CT decomposition, first, the previous iterative results are used to calculate a contribution of the Rayleigh scattering during the iterative process, and then the contribution of the Rayleigh scattering is removed from the original projection data. As a result, a more accurate low-energy dual-energy CT material decomposition method according to the embodiment of the present invention can be obtained.

Figure 3:
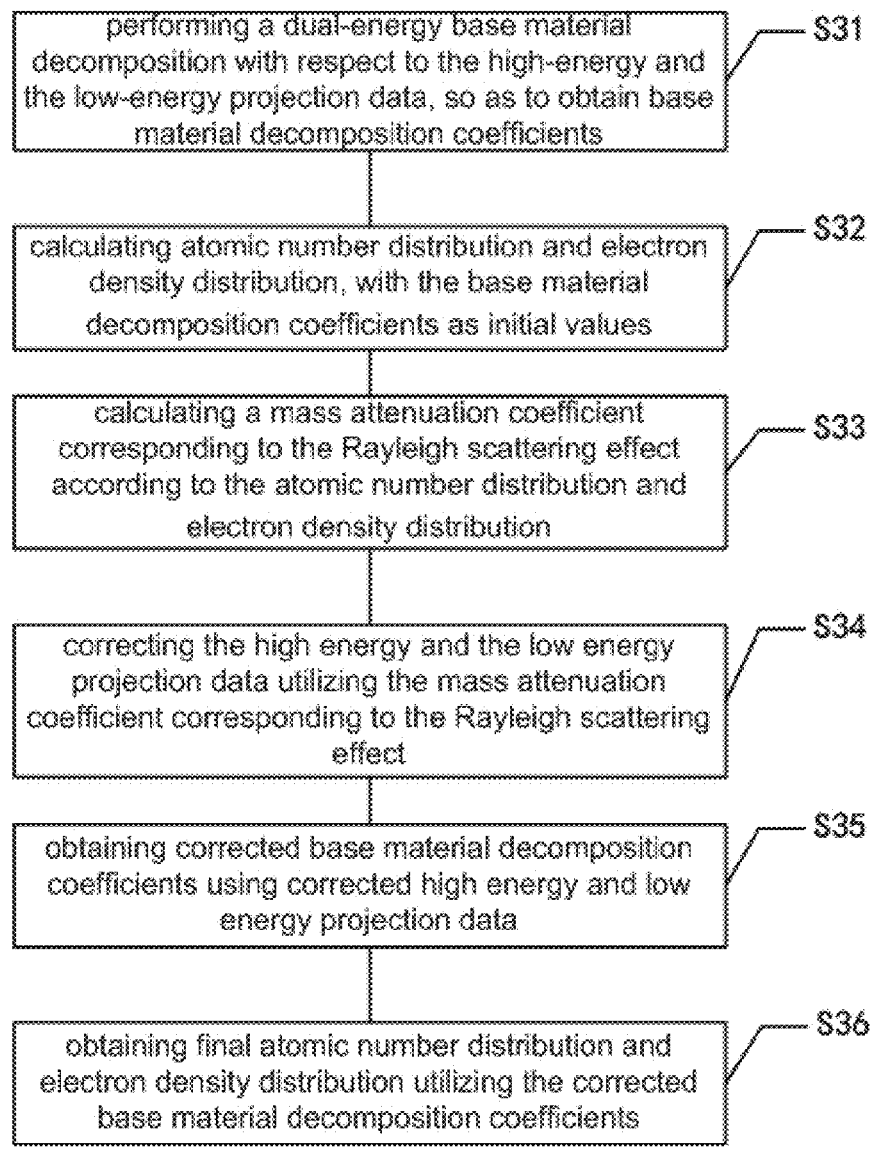
FIG. 3 is a flow diagram of a method for decomposing a material for dual-energy X-ray CT according to another embodiment of the present disclosure.
Figure 4A:
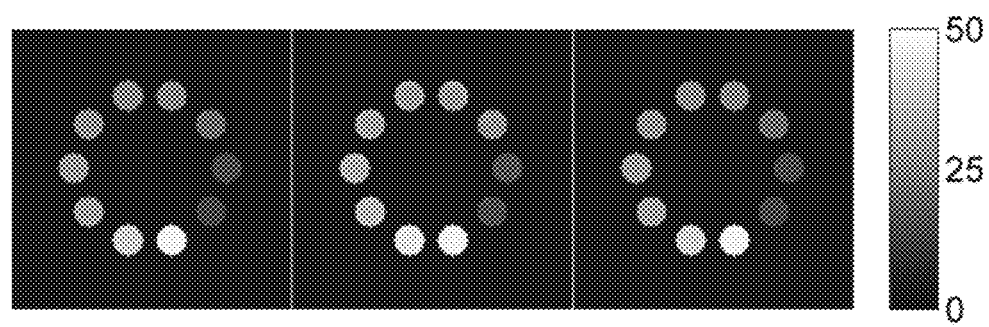
FIG. 4A shows results of a simulated experiment in the embodiment of the present disclosure without noise, wherein the left side shows the true atomic number distribution of the model and the middle portion shows a result of the conventional dual-energy CT-based material decomposition, and the right side shows a result of the decomposition of a dual-energy CT material according to an embodiment of the present disclosure.
Figure 4B:
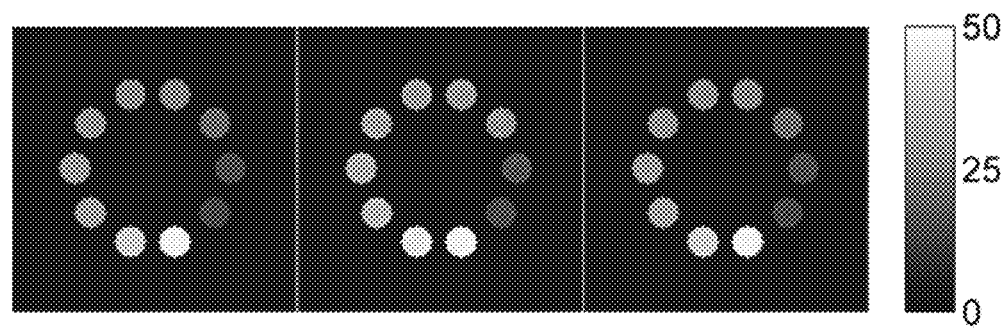
FIG. 4B shows results of a simulated experiment in the embodiment of the present disclosure with Poisson noise, wherein the left side shows an actual atomic number distribution of the model, the middle portion shows a decomposing result of the conventional dual-energy CT base material, and the right side shows a decomposing result of a dual-energy CT material according to an embodiment of the present disclosure.
Figure 5A:
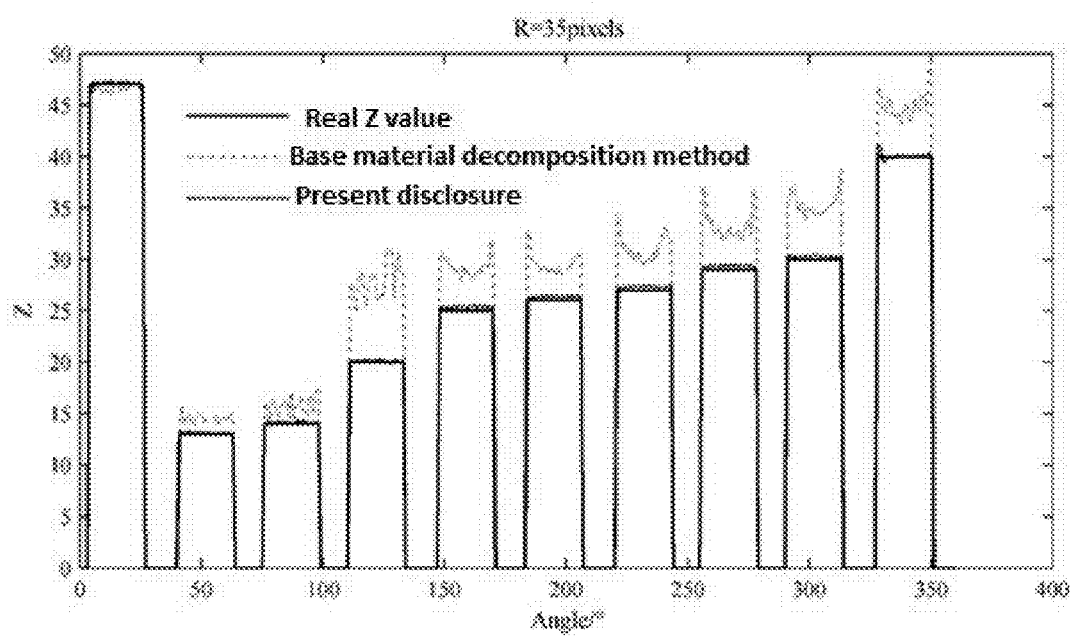
FIG. 5A shows a cross-sectional line drawn along an arc of the center of each cylinder in FIG. 4A, i.e., a real-value curve, a curve obtained by a conventional dual-energy CT base material decomposition method, and a curve obtained by a method of the embodiment method of the present disclosure.
Figure 5B:
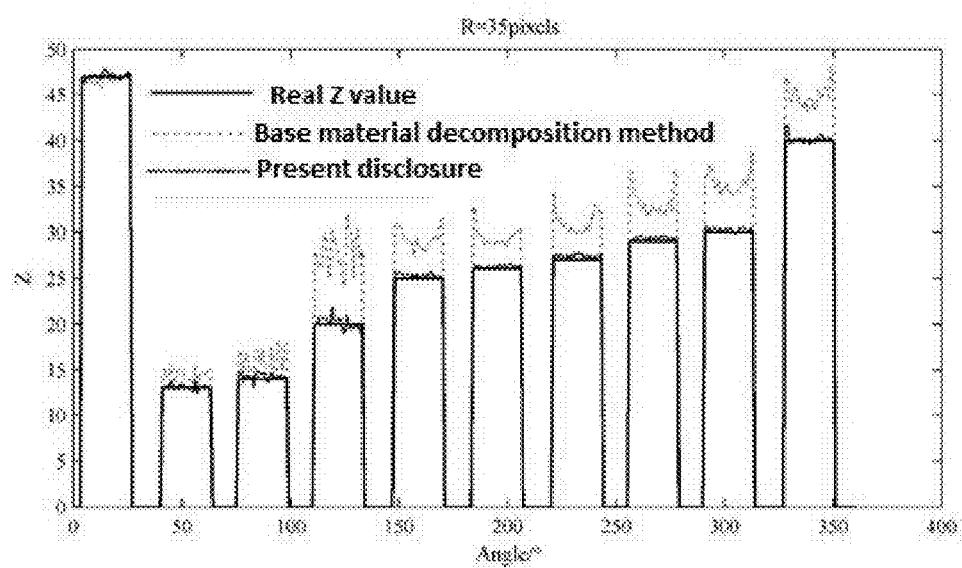
FIG. 5B shows a cross-sectional line drawn along an arc of the center of each cylinder in FIG. 4B, i.e., a real-value curve, a curve obtained by a conventional dual-energy CT base material decomposition method, and a curve obtained by a method of the embodiment method of the present disclosure.

FIG. 3 is a flow diagram of a method for decomposing a material for dual-energy X-ray CT according to another embodiment of the present disclosure, where the dual-energy X-ray CT performing a dual-energy X-ray scanning on an object to be inspected to obtain a high energy projection data and a low energy projection data. At a step of S31, a dual-energy X-ray CT scan is performed on the object to be inspected to obtain high-energy projection data and low-energy projection data. At a step of S32, atomic number distribution and electron density distribution for the object to be inspected are calculated, with the base material decomposition coefficients as initial values.

Different from the embodiment as shown in FIG. 2, at a step of S33, the mass attenuation coefficient corresponding to the Rayleigh scattering effect is calculated according to the atomic number distribution and electron density distribution. For example, the calculation method may be expressed by Klein-Nishina scattering cross-sectional theoretical formula multiplied with the scale factor of the elastic collision or the other calculation method; and at a step of S34, the high energy projection data and the low energy projection data are corrected by utilizing the mass attenuation coefficient corresponding to the Rayleigh scattering effect, to remove a portion of the high energy projection data and the low energy projection data corresponding to the Rayleigh scattering effect; and at a step of S35, corrected base material decomposition coefficients are obtained using corrected high energy projection data and low energy projection data. At a step of S36, final atomic number distribution and electron density distribution for the object to be inspected are obtained utilizing the corrected base material decomposition coefficients.

FIGS. 4A, 4B, 5A and 5B show simulation results of embodiments of the present disclosure. During the simulation, a numerical model containing 10 cylinders was used, and the atomic numbers within the ten cylinders are 13, 14, 20, 25, 26, 27, 29, 30, 40 and 47, respectively. The two types of base materials are selected as carbon and tin with an atomic number of 6 and 50, respectively. During the process of the dual-energy scanning, the X-ray beam generated by electrons with energies of 9 MeV and 6 MeV bombarding the tungsten target was selected as the high and low energy X-ray sources, and meanwhile, a filter was used to filter out photons with energies less than 100 keV. During a process of fan beam scanning, one projection is collected every one degree, a total of 360 projection data are collected; the number of detectors is 193, and the reconstructed image is 128*128. In the simulation, the results of the decomposition of the dual-energy CT are verified and compared for the noiseless projection data. At the same time, the Poisson noise is introduced and the similar method is verified and compared considering the total number of incidence photons are $10^9$.

From the simulation results of FIGS. 4A, 4B, 5A and 5B, it can be found that the technique of the embodiment of the present disclosure can effectively improve the material decomposition accuracy of the conventional dual-energy X-ray CT. The decomposition error caused by the inconsistency of dual-energy CT imaging model with the physical process, which is of practical significance to improve the imaging quality and material identification accuracy of the current dual-energy CT.

There are some inconsistencies between the conventional dual-energy X-ray CT imaging model and the material decomposition method and the real physical process, that is, there is a plurality of types of interactions between X-photon and substance, and the conventional dual-energy CT material decomposition method can only choose two types and ignore the others. The dual-energy X-ray CT iterative material decomposition method of the above-described embodiments of the present disclosure can calculate and remove the influence of other secondary cross section (leaving only two dominant cross-sections), thereby using the corrected high and low energy project data to achieve more accurate material decomposition and material identification. The technology of the embodiment of the disclosure can be applied to the dual-energy X-ray CT system of various fields, including clinical therapy (such as Siemens dual source CT, GE high voltage fast switching dual-energy CT, Philips double detector, security inspection, anti-smuggling, industrial non-destructive testing or the like, regardless of low energy (several hundred keV) or high energy (more than a few MeV). The present disclosure may effectively improve the dual-energy CT material identification accuracy, reduce effectively improve improper reporting rate and false reporting rate, which has a significant market value.

The above detailed descriptions have illustrated embodiments of the X-ray imaging system and method by block diagrams, flowcharts and/or examples. In a case where such a block diagram, flowchart and/or example includes one or more functions and/or operations, it is to be understood by those skilled in the art that each of the functions and/or operations in the block diagram, flowchart and/or example may be implemented by various hardware, software, or firmware alone and/or any combination thereof. In an embodiment, some parts of the subject matter described in embodiments of the present disclosure may be implemented by Application Specific Integrated Circuits (ASICs), Field Programmable Gate Arrays (FPGAs), Digital Signal Processors (DSPs) or other integrated formats. However, those skilled in the art will appreciate that some aspects of the embodiments disclosed herein, partially or as a whole, may be equally implemented by an Integrated Circuit, one or more computer programs running on one or more computers (for example, one or more programs running on one or more computer systems), one or more programs running on one or more processors (for example, one or more programs running on one or more microprocessors), firmware, or any combination thereof. One skilled person in the art has the ability of designing a circuitry and/or writing software and/or firmware codes according to the present disclosure. Further, it is to be understood by those skilled in the art that the mechanism of the subject matter of the present disclosure may be distributed in various forms of program products, and that all embodiments are applicable regardless of specific types of signal carrying media which are used to carry out the distribution. Examples of the signal carrying media include, but not limited to, recordable media such as floppy disk, hard disk driver, compact disk (CD), digital versatile disk (DVD), digital tape, or computer memory, or transmission type media such as digital and/or analog communication media (for example, fiber cable, waveguide, wired communication link, wireless communication like, or the like).

Though the present disclosure is described by referring to some embodiments thereof, it is to be understood that terminologies used herein are illustrative, not in a limiting sense. The present disclosure may be implemented in various forms without departing from the spirit or substance of the present disclosure. Therefore, it is to be understood that the above embodiments are not intended to be limited by the foregoing details, and should be interpreted broadly in the spirit and scope as defined in the following claims. All changes and modifications falling in the scope of the claims and equivalents thereof are to be covered by the following claims.

We claim:

1. A method for performing material decomposition using a dual-energy X-ray CT, the dual-energy X-ray CT performing a dual-energy X-ray scanning on an object to be inspected to obtain a high energy projection data and a low energy projection data, the method comprising steps of:

performing a dual-energy base material decomposition with respect to the high-energy projection data and the low-energy projection data, so as to obtain base material decomposition coefficients;

calculating atomic number distribution and electron density distribution for the object to be inspected, with the base material decomposition coefficients as initial values;

calculating a mass attenuation coefficient corresponding to the photoelectric effect according to the atomic number distribution and electron density distribution;

correcting the high energy projection data and the low energy projection data utilizing the mass attenuation coefficient corresponding to the photoelectric effect to remove a portion of the high energy projection data and the low energy projection data corresponding to the photoelectric effect;

obtaining corrected base material decomposition coefficients using corrected high energy projection data and low energy projection data; and obtaining final atomic number distribution and electron density distribution for the object to be inspected utilizing the corrected base material decomposition coefficients.

2. The method according to claim 1, wherein the step of obtaining final atomic number distribution and electron density distribution for the object to be inspected utilizing the corrected base material decomposition coefficients further comprises:

determining whether the corrected base material decomposition coefficients satisfy an iteration convergence criterion;

on the condition that the corrected base material decomposition coefficients satisfy the iteration convergence criterion, calculating corrected atomic number distribution and electron density distribution for the object to be inspected as the final atomic number distribution and electron density distribution by utilizing the corrected base material decomposition coefficients.

3. The method according to claim 1, further comprising:
on the condition that the corrected base material decomposition coefficients do not satisfy the iteration convergence criterion, iterating with the corrected base material decomposition coefficients as the initial values until the iteration convergence criterion is satisfied by further corrected base material decomposition coefficients;
calculating corrected atomic number distribution and electron density distribution for the object to be inspected as the final atomic number distribution and electron density distribution by utilizing the further corrected base material decomposition coefficients that satisfy the iteration convergence criterion.

4. The method according to claim 1, wherein the final atomic number distribution and electron density distribution include equivalent atomic number and electron density for each pixel.

5. The method according to claim 1, wherein the base material decomposition coefficients are reconstructed using filtering back projection or algebra reconstruction technique iterative algorithms.

6. A method for performing material decomposition using a dual-energy X-ray CT, the dual-energy X-ray CT performing a dual-energy X-ray scanning on an object to be inspected to obtain a high energy projection data and a low energy projection data, the method comprising steps of:
performing a dual-energy base material decomposition with respect to the high-energy projection data and the low-energy projection data, so as to obtain base material decomposition coefficients;
calculating atomic number distribution and electron density distribution for the object to be inspected, with the base material decomposition coefficients as initial values;
calculating a mass attenuation coefficient corresponding to the Rayleigh scattering effect according to the atomic number distribution and electron density distribution;
correcting the high energy projection data and the low energy projection data utilizing the mass attenuation coefficient corresponding to the Rayleigh scattering effect to remove a portion of the high energy projection data and the low energy projection data corresponding to the Rayleigh scattering effect;
obtaining corrected base material decomposition coefficients using corrected high energy projection data and low energy projection data; and
obtaining final atomic number distribution and electron density distribution for the object to be inspected utilizing the corrected base material decomposition coefficients.

7. The method according to claim 6, wherein the step of obtaining final atomic number distribution and electron density distribution for the object to be inspected utilizing the corrected base material decomposition coefficients further comprises:
determining whether the corrected base material decomposition coefficients satisfy an iteration convergence criterion;
on the condition that the corrected base material decomposition coefficients satisfy the iteration convergence criterion, calculating corrected atomic number distribution and electron density distribution for the object to be inspected as the final atomic number distribution and electron density distribution by utilizing the corrected base material decomposition coefficients.

8. The method according to claim 6, further comprising:
on the condition that the corrected base material decomposition coefficients do not satisfy the iteration convergence criterion, iterating with the corrected base material decomposition coefficients as the initial values until the iteration convergence criterion is satisfied by further corrected base material decomposition coefficients;
calculating corrected atomic number distribution and electron density distribution for the object to be inspected as the final atomic number distribution and electron density distribution by utilizing the further corrected base material decomposition coefficients that satisfy the iteration convergence criterion.

9. The method according to claim 6, wherein the final atomic number distribution and electron density distribution include equivalent atomic number and electron density for each pixel.

10. The method according to claim 6, wherein the base material decomposition coefficients are reconstructed using filtering back projection or algebra reconstruction technique iterative algorithms.

11. A dual-energy X-ray CT apparatus comprising:
an X-ray source configured to perform a dual-energy X-ray scanning on an object to be inspected;
a detecting and collecting device configured to receive dual-energy X-rays passing through the object to be inspected so as to generate a high energy projection data and a low energy projection data;
a calculation unit configured to perform the following operations:
performing a dual-energy base material decomposition with respect to the high-energy projection data and the low-energy projection data, so as to obtain base material decomposition coefficients;
calculating atomic number distribution and electron density distribution for the object to be inspected, with the base material decomposition coefficients as initial values;
calculating a mass attenuation coefficient corresponding to the photoelectric effect according to the atomic number distribution and electron density distribution;
correcting the high energy projection data and the low energy projection data utilizing the mass attenuation coefficient corresponding to the photoelectric effect to remove a portion of the high energy projection data and the low energy projection data corresponding to the photoelectric effect;
obtaining corrected base material decomposition coefficients using corrected high energy projection data and low energy projection data; and
obtaining final atomic number distribution and electron density distribution for the object to be inspected utilizing the corrected base material decomposition coefficients.

12. The apparatus according to claim 11, wherein the calculation unit is further configured to:
determine whether the corrected base material decomposition coefficients satisfy an iteration convergence criterion;
on the condition that the corrected base material decomposition coefficients satisfy the iteration convergence criterion, calculate corrected atomic number distribution and electron density distribution for the object to be inspected as the final atomic number distribution and electron density distribution by utilizing the corrected base material decomposition coefficients.

13. The apparatus according to claim 12, wherein the calculation unit is further configured to:
   on the condition that the corrected base material decomposition coefficients do not satisfy the iteration convergence criterion, iterate with the corrected base material decomposition coefficients as the initial values until the iteration convergence criterion is satisfied by further corrected base material decomposition coefficients;
   calculate corrected atomic number distribution and electron density distribution for the object to be inspected as the final atomic number distribution and electron density distribution by utilizing the further corrected base material decomposition coefficients that satisfy the iteration convergence criterion.

14. The apparatus according to claim 11, wherein the final atomic number distribution and electron density distribution include equivalent atomic number and electron density for each pixel.

15. The apparatus according to claim 11, wherein the calculation unit is configured to reconstruct the base material decomposition coefficients using filtering back projection or algebra reconstruction technique iterative algorithms.

16. A dual-energy X-ray CT apparatus comprising:
   an X-ray source configured to perform a dual-energy X-ray scanning on an object to be inspected;
   a detecting and collecting device configured to receive dual-energy X-rays passing through the object to be inspected so as to generate a high energy projection data and a low energy projection data;
   a calculation unit configured to perform the following operations:
      performing a dual-energy base material decomposition with respect to the high-energy projection data and the low-energy projection data, so as to obtain base material decomposition coefficients;
      calculating atomic number distribution and electron density distribution for the object to be inspected, with the base material decomposition coefficients as initial values;
      calculating a mass attenuation coefficient corresponding to the Rayleigh scattering effect according to the atomic number distribution and electron density distribution;
      correcting the high energy projection data and the low energy projection data utilizing the mass attenuation coefficient corresponding to the Rayleigh scattering effect to remove a portion of the high energy projection data and the low energy projection data corresponding to the Rayleigh scattering effect;
      obtaining corrected base material decomposition coefficients using corrected high energy projection data and low energy projection data; and
      obtaining final atomic number distribution and electron density distribution for the object to be inspected utilizing the corrected base material decomposition coefficients.

17. The apparatus according to claim 6, wherein the calculation unit is further configured to:
   determine whether the corrected base material decomposition coefficients satisfy an iteration convergence criterion;
   on the condition that the corrected base material decomposition coefficients satisfy the iteration convergence criterion, calculate corrected atomic number distribution and electron density distribution for the object to be inspected as the final atomic number distribution and electron density distribution by utilizing the corrected base material decomposition coefficients.

18. The apparatus according to claim 17, wherein the calculation unit is further configured to:
   on the condition that the corrected base material decomposition coefficients do not satisfy the iteration convergence criterion, iterate with the corrected base material decomposition coefficients as the initial values until the iteration convergence criterion is satisfied by further corrected base material decomposition coefficients;
   calculate corrected atomic number distribution and electron density distribution for the object to be inspected as the final atomic number distribution and electron density distribution by utilizing the further corrected base material decomposition coefficients that satisfy the iteration convergence criterion.

19. The apparatus according to claim 16, wherein the final atomic number distribution and electron density distribution include equivalent atomic number and electron density for each pixel.

20. The apparatus according to claim 16, wherein the calculation unit is configured to reconstruct the base material decomposition coefficients using filtering back projection or algebra reconstruction technique iterative algorithms.

* * * * *